United States Patent [19]
Chang et al.

[11] Patent Number: 5,945,288
[45] Date of Patent: Aug. 31, 1999

[54] METHOD FOR CLONING AND PRODUCING THE PMEI RESTRICTION ENDONUCLEASE

[75] Inventors: Zhiyuh Chang, New Rochelle, N.Y.; Richard D. Morgan, Middleton, Mass.

[73] Assignee: New England Biolabs, Inc., Beverly, Mass.

[21] Appl. No.: 08/976,703

[22] Filed: Nov. 24, 1997

[51] Int. Cl.$^6$ .................................................. C12Q 1/68
[52] U.S. Cl. .......................... 435/6; 435/320.1; 536/23.7
[58] Field of Search ................... 435/6, 320.1; 536/23.7

[56] References Cited

U.S. PATENT DOCUMENTS

| | | | |
|---|---|---|---|
| 5,196,330 | 3/1993 | Morgan et al. | 435/199 |
| 5,200,333 | 4/1993 | Wilson | 435/172.3 |

OTHER PUBLICATIONS

Kosykh, et al., Molec. Gen. Genet., 178:717–718 (1980).
Mann, et al., Gene, 3:97–112 (1978).
Walder, et al., Proc. Nat. Acad. Sci., 78:1503–1507 (1981).
Bougueleret, et al., Nucl. Acid Res., 12:3659–3676 (1984).
Gingeras and Brooks, Proc. Natl. Acad. Sci. USA 80:402–406 (1983).
Theriault and Roy, Gene, 19:355–359 (1982).
Blumenthal, et al., J. Bacteriol., 164:501–509 (1985).
Kiss, et al., Nucl. Acid Res., 13:6403–6421 (1985).
Szomolanyi, et al, Gene, 10:219–225 (1980).
Janulaitis, et al., Gene, 20:197–204 (1982).
Kiss and Baldauf, Gene, 21:111–119 (1983).
Walder, et al., (J. Biol. Chem., 258:1235–1241 (1983).
Piekarowicz, et al., Nucleic Acid Res. 19:1831–1835 (1991).
Piekarowicz, et al., J. Bacteriology, 173:150–155 (1991).
Fomenkov, et al., Nucleic Acids Res. 22:2399–2403 (1994).
Lunnen, et al., Gene, 74:25–32 (1988).
Raleigh and Wilson, Proc. Natl. Acad. Sci, USA, 83:9070–9074 (1986).
Heitman and Model, J. Bact., 196:3243–3250 (1987).
Raleigh, et al., Genetics, 122:279–296 (1989).
Waite–Rees, et al., J. Bacteriology, 173:5207–5219 (1991).
Fuller, Gene 19:43–54 (1982).
Shimatake and Rosenberg, Nature, 254:128 (1981).
Shine & Dalgarno, Proc. Natl. Acad. Sci. USA, 71:1342–1346 (1974).
Ikemura, J. Mol. Biol., 151:389–409 (1981).
Matsudaira, J. Biol. Chem., 262:10035–10038 (1987).
Looney, et al., Gene 80:193–208 (1989).

*Primary Examiner*—Scott W. Houtteman
*Attorney, Agent, or Firm*—Gregory D. Williams

[57] ABSTRACT

The present invention relates to recombinant DNA which encodes the PmeI restriction endonuclease and modification methylase, and production of PmeI restriction endonuclease from the recombinant DNA.

7 Claims, 1 Drawing Sheet

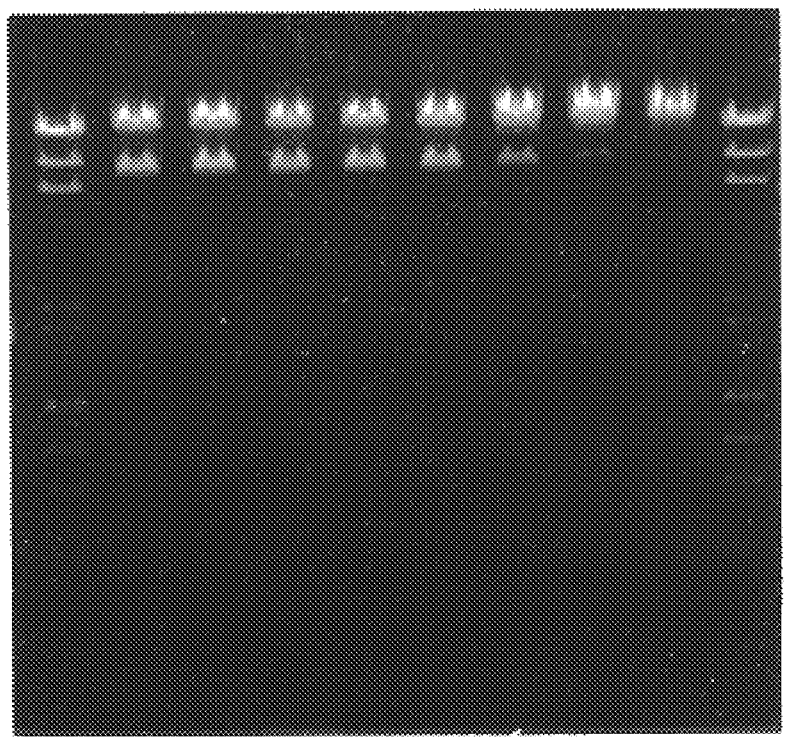
PmeI RESTRICTION ACTIVITY FROM THE E.coli STRAIN NEB #1081

METHOD FOR CLONING AND PRODUCING THE PMEI RESTRICTION ENDONUCLEASE

BACKGROUND OF THE INVENTION

The present invention relates identification of the PmeI restriction endonuclease, obtainable from *Pseudomonas mendocina* (NEB#698) and to the recombinant DNA which encodes the PmeI restriction endonuclease, and the production of PmeI restriction endonuclease from the recombinant DNA.

Type II restriction endonucleases are a class of enzymes that occur naturally in bacteria. When they are purified away from other bacterial components, restriction endonucleases can be used in the laboratory to cleave DNA molecules into precise fragments for molecular cloning and gene characterization.

Restriction endonucleases act by recognizing and binding to particular sequences of nucleotides (the 'recognition sequence') along the DNA molecule. Once bound, they cleave the molecule within, or to one side of, the recognition sequence. Different restriction endonucleases have affinity for different recognition sequences. Over one hundred and eighty restriction endonucleases with unique specificities have been identified among the many hundreds of bacterial species that have been examined to date.

Bacteria tend to possess at most, only a small number of restriction endonucleases per species. The endonucleases typically are named according to the bacteria from which they are derived. Thus, the species *Deinococcus radiophilus* for example, synthesizes three different restriction endonucleases, named DraI, DraII and DraIII. These enzymes recognize and cleave the sequences TTAAA, PuGGNCCPy and CACNNNGTG, respectively. *Escherichia coli* RY13, on the other hand, synthesizes only one enzyme, EcoRI, which recognizes the sequence GAATTC.

It is thought that in nature, restriction endonucleases play a protective role in the welfare of the bacterial cell. They enable bacteria to resist infection by foreign DNA molecules like viruses and plasmids that would otherwise destroy or parasitize them. They impart resistance by cleaving invading foreign DNA molecule each time that the recognition sequence occurs. The cleavage that takes place disables many of the infecting genes and renders the DNA susceptible to further degradation by non-specific nucleases.

A second component of bacterial protective systems are the modification methylases. These enzymes are complementary to restriction endonucleases and they provide the means by which bacteria are able to protect their own DNA and distinguish it from foreign, infecting DNA. Modification methylases recognize and bind to the same recognition sequence as the corresponding restriction endonuclease, but instead of cleaving the DNA, they chemically modify one or other of the nucleotides within the sequence by the addition of a methyl group. Following methylation, the recognition sequence is no longer cleaved by the restriction endonuclease. The DNA of a bacterial cell is always modified by virtue of the activity of its modification methylase. It is therefore insensitive to the presence of the endogenous restriction endonuclease. It is only unmodified, and therefore identifiably foreign DNA, that is sensitive to restriction endonuclease recognition and cleavage.

With the advent of genetic engineering technology, it is now possible to clone genes and to produce the proteins and enzymes that they encode in greater quantities than are obtainable by conventional purification techniques. The key to isolating clones of restriction endonuclease genes is to develop a simple and reliable method to identify such clones within complex 'libraries', i.e. populations of clones derived by 'shotgun' procedures, when they occur at frequencies as low as $10^{-3}$ to $10^{-4}$. Preferably, the method should be selective, such that the unwanted majority of clones are destroyed while the desirable rare clones survive.

Type II restriction-modification systems are being cloned with increasing frequency. The first cloned systems used bacteriophage infection as a means of identifying or selecting restriction endonuclease clones (EcoRII: Kosykh et al., *Molec. Gen. Genet* 178:717–719 (1980); Hhall: Mann et al., *Gene* 3:97–112 (1978); PstI: Walder et al., *Proc. Nat. Acad. Sci.* 78:1503–1507 (1981)). Since the presence of restriction-modification systems in bacteria enable them to resist infection by bacteriophages, cells that carry cloned restriction-modification genes can, in principle, be selectively isolated as survivors from libraries that have been exposed to phage. This method has been found, however, to have only limited value. Specifically, it has been found that cloned restriction-modification genes do not always manifest sufficient phage resistance to confer selective survival.

Another cloning approach involves transferring systems initially characterized as plasmid-borne into *E. coli* cloning plasmids (EcoRV: Bougueleret et al., *Nucl. Acid. Res.* 12:3659–3676 (1984); PaeR7: Gingeras and Brooks, *Proc. Natl. Acad. Sci. USA* 80:402–406 (1983); Theriault and Roy, *Gene* 19:355–359 (1982); PvuII: Blumenthal et al., *J. Bacteriol* 164:501–509 (1985)).

A third approach which is being used to clone a growing number of systems, involves selection for an active methylase gene (U.S. Pat. No. 5,200,333 and BsuRI: Kiss et al., *Nucl. Acid. Res.* 13:6403–6421 (1985)). Since restriction and modification genes are often closely linked, both genes can often be cloned simultaneously. This selection does not always yield a complete restriction system however, but instead yields only the methylase gene (BspRI: Szomolanyi et al., *Gene* 10:219–225 (1980); Bcn I: Janulaitis et al, *Gene* 20:197–204 (1982); Bsu RI: Kiss and Baldauf, *Gene* 21:111–119 (1983); and Msp I: Walder et al., *J. Biol. Chem.* 258:235–1241 (1983)).

Another method for cloning methylase and endonuclease genes is based on a colorimetric assay for DNA damage (U.S. Pat. No. 5,498,535). When screening for a methylase, the plasmid library is transformed into the host *E. coli* strain such as AP1-200. The expression of a methylase will induce the SOS response in an *E. coli* strain which is McrA$^+$, McrBC$^+$, or Mrr$^+$. The AP1-200 strain is temperature sensitive for the Mcr and Mrr systems and includes a lac-Z gene fused to the damage inducible dinD locus of *E. coli*. The detection of recombinant plasmids encoding a methylase or endonuclease gene is based on induction at the restrictive temperature of the lacZ gene. Transformants encoding methylase genes are detected on LB agar plates containing X-gal as blue colonies. (Piekarowicz, et.al., *Nucleic Acids Res.* 19:1831–1835 (1991) and Piekarowicz, et.al. *J. Bacteriology* 173:150–155 (1991)). Likewise, the *E. coli* strain ER1992 contains a dinD1-Lac Z fusion but is lacking the methylation dependent restriction systems McrA, McrBC and Mrr. In this system (called the "endoblue" method), the endonuclease gene can be detected in the absence of it's cognate methylase when the endonuclease damages the host cell DNA, inducing the SOS response. The SOS-induced cells form deep blue colonies on LB agar plates supplemented with X-gal. (Xu et.al. *Nucleic Acids Res.* 22:2399–2403 (1994)).

Sometimes the straight-forward methylase selection method fails to yield a methylase (and/or endonuclease)

clone due to various obstacles. See, e.g., Lunnen, et al., *Gene*, 74(1):25–32 (1988). One potential obstacle to cloning restriction-modification genes lies in trying to introduce the endonuclease gene into a host not already protected by modification. If the methylase gene and endonuclease gene are introduced together as a single clone, the methylase must protectively modify the host DNA before the endonuclease has the opportunity to cleave it. On occasion, therefore, it might only be possible to clone the genes sequentially, methylase first then endonuclease.

Another obstacle to cloning restriction-modification systems lies in the discovery that some strains of *E. coli* react adversely to cytosine or adenine modification; they possess systems that destroy DNA containing methylated cytosine (Raleigh and Wilson, *Proc. Natl. Acad. Sci., USA* 83:9070–9074 (1986)) or methylated adenine (Heitman and Model, *J. Bact.* 196:3243–3250 (1987); Raleigh, Trimarchi, and Revel, *Genetics,* 122:279–296 (1989) Waite-Rees, et al., *J. Bacteriology,* 173:5207–5219 (1991)). Cytosine-specific or adenine-specific methylase genes cannot be cloned easily into these strains, either on their own, or together with their corresponding endonuclease genes. To avoid this problem it is necessary to use mutant strains of *E. coli* (McrA$^-$ and McrB$^-$ or Mrr$^-$) in which these systems are defective.

A third potential difficulty is that some restriction endonuclease and methylase genes may not express in *E. coli* due to differences in the transcription machinery of the source organism and *E. coli*, such as differences in promoter and ribosome binding sites. The methylase selection technique requires that the methylase express well enough in *E. coli* to fully protect at least some of the plasmids carrying the gene.

Because purified restriction endonucleases, and to a lesser extent, modification methylases, are useful tools for characterizing genes in the laboratory, there is a commercial incentive to obtain bacterial strains through recombinant DNA techniques that synthesize these enzymes in abundance. Such strains would be useful because they would simplify the task of purification as well as providing the means for production in commercially useful amounts.

SUMMARY OF THE INVENTION

The present invention relates to recombinant DNA encoding the genes for the PmeI restriction endonuclease (NEB #560), an enzyme which recognizes the DNA sequence 5' GTTAAAC 3' and cleaves at the middle of the recognition sequence between the third T and first A residue to produce blunt ends, as well as related methods for the production of this enzyme from the recombinant DNA. This invention also relates to a transformed host which expresses the restriction endonuclease PmeI. PmeI restriction endonuclease produced in accordance with the present invention is substantially pure and free of contaminants normally found in restriction endonuclease preparations made by conventional techniques.

DESCRIPTION OF THE DRAWINGS

FIG. 1 is a photograph of an agarose gel demonstrating PmeI restriction endonuclease activity in cell extracts of *E. coli* ER2426 carrying the PmeI endonuclease on the pRRS derived plasmid pRRSPmeIR1 and the DraI methylase on the pACYC184 derived plasmid pACYC184DraIM10. 0.5 gram of cell paste was suspended in 1.5 ml of sonication buffer (20 mM Tris-HCl, 1 mM dithiothreitol, 0.1 mM EDTA, pH 7.5), broken by sonication and clarified by centrifugation. The extract was used to digest 1 µg of λ DNA per 50 µl reaction volume in 1×NEBuffer 4, supplemented with 100 µg/ml BSA and incubation at 37° C. for one hour. Lanes 1 and 10: HindIII-λ+HaeIII-φX174 size standard; Lane 2: 0.01 µl crude extract; Lane 3: 5×10$^{-3}$ µl crude extract; Lane 4: 2.5×10$^{-3}$ µl crude extract; Lane 5: 1.25× 10$^{-3}$ µl crude extract; Lane 6: 6.25×10$^{-4}$ µl crude extract; Lane 7: 3.13×10$^{-4}$ µl crude extract; Lane 8: 1.56×10$^{-4}$ µl crude extract; Lane 9: 7.81×10$^{-5}$ µl crude extract. Total PmeI activity corresponds to approximately 1×10$^7$ units per gram cell paste.

DETAILED DESCRIPTION OF THE INVENTION

The present invention relates to recombinant DNA which encodes the PmeI restriction endonuclease, as well as to methods of producing recombinant PmeI enzyme.

The cloning of the PmeI restriction endonuclease gene from *Pseudomonas mendocina* proved to be unusually difficult.

The methylase selection method (U.S. Pat. No. 5,200, 333) was vigorously attempted but failed to yield a PmeI methylase producing clone. Even after cloning of the PmeI endonuclease gene, conserved methylase motifs have not been located adjacent to the PmeI endonuclease gene. This lack of a PmeI methylase gene significantly complicated the cloning of the corresponding endonuclease gene.

In order to clone the PmeI restriction endonuclease gene, it was decided to obtain highly purified PmeI restriction endonuclease protein from *Pseudomonas mendocina* cells to determine amino acid sequence at the N-terminus of the endonuclease. The amino acid sequence was then used to design degenerate oligonucleotide primers for PCR amplification of this region of DNA from genomic *Pseudomonas mendocina* DNA. The sequence of the small PCR amplified DNA was then used to design non-degenerate inverse PCR primers, which were used to amplify DNA flanking the start of the PmeI endonuclease gene using inverse PCR technologies. Two such amplified products, a 1.4 kb product from BssHII digested and circularized *Pseudomonas mendocina* DNA template and a 900 bp product from BsaWI digested and circularized *Pseudomonas mendocina* DNA template were cloned into vector pUC19 and sequenced. The sequence data of an approximately 1.6 kb region of the *Pseudomonas mendocina* genome derived from the amplified products was used to identify the PmeI endonuclease gene. An open reading frame of 693 bp was observed to have N-terminal amino acid sequence matching that determined from sequencing the N-terminus of the purified PmeI endonuclease protein and was therefore identified to be the PmeI endonuclease gene. No obvious known methylase motifs were found in the six frame amino acid translations of both the 700 bp and 190 bp DNA sequence immediately 3' and 5' to the identified PmeI endonuclease gene respectively. In order to find a possible PmeI methylase, DNA sequence data beyond both sides of this 1.6 kb region needed to be obtained. To this end, additional inverse PCR experiments were conducted. An additional 1.57 kb of DNA sequence 3' to the endonuclease and 3.1 kb of sequence 5' to the endonuclease were obtained and no obvious known methylase motifs were found. Several possibilities exist. One of the ORFs adjacent to the endonuclease gene may code for a PmeI methylase, but fail to contain highly homologous methylase motifs allowing it to be identified as such. The methylase could be quite large, and thus more sequence, particularly 3' to the endonuclease, might be needed to locate the gene. The methylase could be located elsewhere on the genomic *Pseudomonas mendocina* DNA and not adjacent to the endonuclease gene. Another possibility is that *Pseudomonas mendocina* DNA does not contain a methylase gene corresponding to the PmeI endonuclease.

Absent a PmeI methylase gene to express to protect the host from the corresponding endonuclease gene, other methylases that potentially could block PmeI restriction activity were investigated. MseI methylase, which recognizes TTAA, the internal four bases of the PmeI recognition sequence, was found to not block PmeI cleavage. A series of oligonucleotides containing a PmeI site was constructed so that one of the adenines or the cytosine in the recognition sequence was methylated and these oligos were subjected to PmeI cleavage to see if PmeI could be blocked by methylation. It was found that methylation at the third adenine residue blocked PmeI cleavage, but not methylation at either the first or second adenine, nor methylation at the C5 position of the cytosine residue. N4 cytosine methylation was not tested. The DraI methylase recognizes the DNA sequence 5'TTTAAA3' which is the internal six bases of the PmeI site 5'GTTTAAAC3'. The DraI methylase could methylate at any one of the three adenines and therefore might or might not block PmeI restriction digestion, so it was necessary to determine whether DNA modified by DraI methylase was resistant to PmeI restriction digestion. To this end, partial Sau3AI subclones of a DraI methylase producing clone, pDraIRM9.7-G2 were cloned into the vector pNEB193, which contains a single PmeI site and four DraI sites and DraI methylase producing clones were selected by the methylase selection method. The plasmids from these clones were isolated and shown to be protected from PmeI as well as DraI restriction. Since DNA modified by DraI methylase was protected from PmeI restriction digestion, the PmeI endonuclease gene could then be expressed in a host pre-protected by DraI methylase. DraI methylase was subsequently cloned into a vector, pACYC184, compatible with expression vectors such as pRRS or pAII17. This was accomplished by cloning Sau3AI partial subclones of pDraIRM9.7-G2 into pACYC184 and the selecting for methylase producing clones by methylase selection.

The PmeI endonuclease was then expressed by amplifying the complete gene from *Pseudomonas mendocina* DNA and cloning it into an expression vector, pRRS. This construct was introduced into a host which was pre-modified at PmeI sites by virtue of the DraI methylase gene carried on the separate compatible plasmid pACYC184. PmeI endonuclease is produced by growing the host containing the PmeI endonuclease gene and DraI methylase gene, inducing with the appropriate expression conditions, harvesting the cells and purifying the PmeI endonuclease.

The method described herein by which the PmeI restriction endonuclease is preferably cloned and expressed is illustrated in FIG. 1 and includes the following steps:

1. *Pseudomonas mendocina* is grown in flasks containing a modified LB medium with no magnesium added at 37° C. with agitation and aeration overnight. The cells are harvested, lysed and the genomic DNA purified.

2. The PmeI restriction endonuclease is purified to near homogeneity from *Pseudomonas mendocina* cells by a combination of protein purification techniques developed at New England Biolabs, Inc. (see Example 1, step 2). The endonuclease so purified is nearly homogeneous on SDS polyacrylamide gel electrophoresis and has an apparent molecular weight of approximately 26 kilodaltons.

3. The amino terminal amino acid sequence of the endonuclease is obtained using an Applied BioSystems Division, Perkin-Elmer Corporation (Foster City, Calif.) 470A Protein Sequencer (Waite-Rees, et al, *J. Bacteriol.* 173:5207–5219 (1991)), and used to direct synthesis of degenerate oligonucleotide primers for amplification of the DNA at the start of the PmeI endonuclease gene from *Pseudomonas mendocina* genomic DNA, and to identify the PmeI endonuclease gene in subsequent studies.

4. A portion of the PmeI endonuclease gene is amplified using degenerate DNA primers based on the amino acid sequence obtained in step 3, one corresponding to the amino acid residues 1 through 6 (M)TTNSP (SEQ ID NO:1) and one corresponding to amino acid residues 10 through 14 MIDEC (SEQ ID NO:2) for the reverse strand of DNA. Individual clones of the amplified DNA are sequenced.

5. *Pseudomonas mendocina* genomic DNA is digested by ApoI, BsaHI, BsrFI, BstYI, EaeI, HaeII, Sau3AI, NlaIII, EagI and BssHII endonucleases and the resulting fragments are ligated at low DNA concentration to favor intramolecular ligation. Primer PmeI-IP1 is designed to anneal in the region between the degenerate primers of step 4 corresponding to amino acid residues Asp-Val-Gly-Met-Ile-Asp (SEQ ID NO:3) and the first nucleotide G of the codon coding for Glu with its 3' end oriented toward the unknown region. Since the DNA sequences of clones obtained in step 4 differed in sequence at the fourth and fifth residues, Asn and Ser, two separate primers are made with primer PmeI-IP2 hybridizing to one class of sequence and primer PmeI-IP3 to the second class of sequence. The circularized fragments containing DNA corresponding to the N-terminus of the PmeI endonuclease gene are amplified using primers PmeI-IP1 and PmeI-IP2 and primers PmeI-IP1 and PmeI-1P3. Amplified products of various sizes are produced and cloned into pUC19 vector.

6. The various pUC19 constructs are sequenced. Only one construct, pUC19BssHII21 containing a 1400 bp amplified fragment from BssHII digested and circularized DNA contains DNA sequence that matches the N-terminal amino acid sequence of the PmeI endonuclease 3' to primer PmeI-IP1. However, primer PmeI-IP3 hybridizes elsewhere likely due to mismatches on the primer sequences. It follows that both primers PmeI-IP2 and PmeI-IP3 are likely to contain mismatches at the sequence for the fourth and fifth residues Asn and Ser.

7. A new set of primers are designed based on the sequence obtained from the pUCBssHII21 clone. The circularized fragments containing DNA corresponding to the N-terminus of the PmeI endonuclease gene are amplified using the new primers. The BsaWI digested and circularized DNA produces a 900 bp product which is cloned into the vector pUC19.

8. The construct, pUC19BsaWI5 containing the amplified 900 bp fragment from the BsaWI digested circular DNA is sequenced. There is an open reading frame matching the N-terminal amino acid sequence data and which is of the correct size to produce a protein of approximately 26 kD. The BsaWI product contains 190 bp 5' to the endonuclease gene and 90 bp 3' to the endonuclease gene. The BssHII product contains 700 bp 3' to the endonuclease gene. No obvious methylase motifs are found in the sequenced region flanking the endonuclease gene. To search for a PmeI methylase gene, DNA flanking both sides of the endonuclease gene is amplified, cloned and sequenced as described in the following sections.

9. *Pseudomonas mendocina* DNA 5' to the PmeI endonuclease gene is amplified in inverse PCR reactions using primers that hybridize near the 5' end of the endonuclease gene. The restriction endonuclease digested and circularized

*Pseudomonas mendocina* DNA prepared in section 5 is used as *Proc. Nat. Acad.* templates. Amplified products are cloned into pUC19 vector.

10. Various pUC19 constructs carrying the amplified products from section 9 are sequenced. BstYI digested and circularized DNA produces a 3.3 kb product and HaeII digested and circularized DNA produces a 0.9 kb product. No obvious methylase motifs can be found in the six frame amino acid translations from approximately 3.1 kb of sequenced DNA 5' to the PmeI endonuclease gene.

11. *Pseudomonas mendocina* DNA 3' to the PmeI endonuclease gene is amplified in two consecutive inverse PCR experiments. *Pseudomonas mendocina* DNA is digested with AatII, HinpII, MscI, MseI, SacI, StuI and Tsp509I endonucleases and the resulting fragments are ligated at low DNA concentration to favor intramolecular ligation. These circular templates as well as the BsaHI digested, circular template from section 5 are used in the first inverse PCR experiment. One of the primers hybridizes to DNAs just outside the 3' terminus of the PmeI endonuclease gene with its 3' end oriented toward the unknown region. The other hybridizes within and near the 3' end of endonuclease gene and is oriented in the opposite direction. The AatII digested, circularized DNA produces a 1.1 kb product; the MscI digested, circular DNA produces a 1.4 kb product, and the BsaHI digested, circular DNA produces a 0.7 kb product. These amplified DNAs are cloned into pUC19 and sequenced. Two more primers based on the newly derived DNA sequence information are synthesized and used in the second inverse PCR experiment. The HaeII digested, circularized DNA (section 5) produces a 0.7 kb product which is cloned into pUC19 and sequenced. Approximately 1.57 kb of DNA 3' to the 3' end of the endonuclease gene thus sequenced contains no obvious methylase motifs.

12. A DraI methylase producing clone, pDraIRM9.7-G2 is partially digested with Sau3AI and the resulting DNA fragments are inserted into pNEB193 vector. Transformants are pooled together, the populations of plasmids are purified and digested with DraI endonuclease. The restricted plasmids are transformed back into *E. coli* to recover uncut clones. Plasmids of nine individual transformants surviving DraI digestion are purified. Eight of the nine plasmids are protected from DraI endonuclease digestion as well as from PmeI endonuclease digestions.

13. Overexpressing the PmeI endonuclease gene:

A. General considerations:

There are a number of ways in which the restriction gene can be overexpressed. The DNA sequence and detailed mapping information help determine the best approach for overexpression of the restriction endonuclease gene.

One approach for overexpression comprises designing primers that hybridize directly at the N-terminus of the restriction endonuclease gene and somewhere downstream (3') of the gene in order to use the polymerase-chain reaction to amplify the entire endonuclease gene. The resulting DNA fragment can be inserted into an expression vector such as pRRS directly downstream of an inducible promoter (lacUV5).

Alternatively, overexpression can be accomplished by inserting a promoter recognized strongly by *E. coli*, such as Ptac on pAGR3 (New England Biolabs, Inc.; Beverly, Mass.) directly in front of the beginning of the restriction endonuclease gene. This may be accomplished by finding convenient restriction sites near the beginning and end of the restriction endonuclease gene and compatible restriction sites near the promoter of pAGR3, and transferring the restriction gene into pAGR3 in line with the Ptac promoter. Other regulated promoters which can be used are PlacUV5 (Fuller, *Gene* 19:43–54 (1982)), and IPL (Shimatake and Rosenberg, *Nature* 254:128 (1981)) on pUC19 and pBR322 derivatives. In addition, a strong ribosome binding site (Shine & Dalgarno, *Proc. Natl. Acad. Sci. USA* 71:342–1346 (1974)) can be placed in front of the gene to increase expression.

To obtain a stable clone which overexpresses the restriction endonuclease, the host is generally pre-protected from restriction endonuclease digestion. In the present invention this is accomplished by cloning the DraI methylase on a separate plasmid. DNA modified by DraI methylase is shown in this application to be resistant to PmeI endonuclease digestion. The plasmid used must be compatible with the expression vector. The methylase also must be produced at a level which will protect the host's genome from digestion by the overexpressed restriction endonuclease gene.

The DNA sequence of the gene can be altered by site-directed mutagenesis or by resynthesizing the gene itself to use codons that are more efficiently utilized in *E. coli* (Ikemura, *J. Mol Biol.* 151:389–409 (1981)).

B. Cloning the DraI methylase in a compatible vector:

The Sau3AI partially digested pDraIRM9.7-G2 DNA fragments from section 12 are ligated into vector pACYC184 previously cleaved with BamHI and dephosphorylated. Transformants are pooled together, the populations of plasmids are purified and digested with DraI endonuclease. The restricted plasmids are transformed back into *E. coli* to recover uncut clones. Plasmids of twelve of the fourteen individual transformants mini-prepped are protected from DraI endonuclease digestion. One such clone designated as pACYC184DraIM10 containing an insert of approximately 3 kb is used for subsequent PmeI endonuclease expression.

C. Expression of PmeI endonuclease:

DNA primers are designed and synthesized to amplify the PmeI endonuclease gene. The forward primer has the following elements: a PstI site to facilitate cloning, a stop codon in frame with the lacZ gene, an *E. coli* consensus strong ribosome binding site, 7 nucleotide spacer sequence between the ribosome binding site and the ATG start codon of the PmeI endonuclease and 24 nucleotides matching the PmeI endonuclease DNA sequence for hybridization. The reverse primer has a BglII site and 21 nucleotides matching *Pseudomonas mendocina* DNA 84 bp 3' to the 3' end of PmeI endonuclease gene for hybridization. The endonuclease gene is amplified from the genomic DNA using these primers. The amplified DNA is cleaved by BglII and PstI and ligated into the expression vector pRRS, which has been previously cleaved by PstI and BamHI endonucleases and gel purified. The ligation reaction is transformed into *E. coli* ER2426 competent cells containing pACYC184DraIM10. Vectors containing inserts of desired size are identified by miniprep procedures. Several clones are grown to mid-log phase and induced with 0.5 mM IPTG for 16 hours. The cells are then harvested by centrifugation, resuspended in sonication buffer, lysed by sonication and the extract assayed for PmeI endonuclease activity. One such PmeI expressing host, designated pRRSPmeIR1/pACYC184DraIM10, is propagated and used to produce PmeI restriction endonuclease.

14. Production: The PmeI endonuclease may be produced from host cells carrying the overexpressed PmeI restriction endonuclease gene by propagation in a fermenter in a rich medium with the appropriate antibiotic selection and induction. The cells are thereafter harvested by centrifugation and disrupted by sonication to produce a crude cell extract containing PmeI restriction endonuclease activity.

15. Purification: The crude cell extract containing the PmeI endonuclease is purified by a combination of protein purification techniques, such as affinity-chromatography or ion-exchange chromatography.

Although the above-outlined steps represent the preferred mode for practicing the present invention, it will be apparent to those skilled in the art that the above described approach can vary in accordance with techniques known in the art.

The following Example is given to illustrate embodiments of the present invention as it is presently preferred to practice. It will be understood that this Example is illustrative, and that the invention is not to be considered as restricted thereto except as indicated in the appended claims.

The references cited above and below are herein incorporated by reference.

EXAMPLE 1

Cloning of the PmeI Restriction Endonuclease Genes

1. DNA purification: 5 g of *Pseudomonas mendocina* (NEB #698) cell paste was resuspended by gentle shaking in 20 ml of 25% sucrose, 0.05 M Tris-HCl, 1 mM EDTA, pH 8.0. 5 ml of 0.5 M EDTA, pH 8.0 and 6 ml of freshly prepared 10 mg/ml lysozyme in 0.25 M Tris-HCl pH 8.0 was added and the solution was incubated at 4° C. for 2 hours. 24 ml of Lysis mix (1% Triton-X100, 50 mM Tris, 62.5 mM EDTA, pH 8.0) was added followed by 5 ml of 10% SDS and the solution was incubated at 4° C. overnight. The solution was extracted with 50 ml of equilibrated phenol, the aqueous phase was recovered and extracted with 50 ml of chloroform two times. The aqueous solution was dialyzed against four changes of 2 L of 10 mM Tris, 1 mM EDTA, pH 8.0 overnight. The dialyzed solution was then digested with RNase (100 ug/ml) at 37° C. for 1 hour. The DNA was precipitated by the addition of 1/10th volume 5M NaCl and 0.55 volume of 2-propanol and spooled onto a glass rod. The DNA was air dried and then dissolved in 10 ml of 10 mM Tris, 1 mM EDTA, pH 8.0.

2. Purification of the PmeI restriction endonuclease from *Pseudomonas mendocina* (NEB #698): PmeI restriction enzyme may be produced from NEB #698 by propagation of *Pseudomonas mendocina* cells in a modified LB medium containing no magnesium at 37° C. with agitation and aeration overnight. The cells were harvested by centrifugation. All of the following procedures were performed on ice or at 4° C. 196 g of cell pellet (wet weight) was resuspended in 600 ml 10 of buffer A (20 mM Tris-HCl, 1 mM Dithiothreitol (DTT), 0.1 mM EDTA, 5% glycerol, pH 7.4) containing 50 mM NaCl (buffer A.05), followed by an addition of phenylmethylsulfonyl fluoride (PMSF) to a final concentration of 25 ug/ml. The cell suspension was then broken by sonication. The extract was centrifuged at 12 K rpm for 90 minutes and the supernatant was collected. The pellets were rinsed with 50 ml of buffer A.05 and centrifuged again at 15 K rpm for 90 minutes. The supernatant was combined together (700 ml total) and loaded onto a 216 ml Q-sepharose column (Pharmacia; Piscataway, N.J.) equilibrated with buffer A.05. This column was washed with 200 ml of buffer A.05 and the PmeI activity was eluted with the flow through and the wash. PmeI containing fractions were pooled together and loaded onto a 216 ml heparin-sepharose column (Pharmacia; Piscataway, N.J.) equilibrated in buffer A.05, washed with 600 ml of buffer A.05 and then a 2 L linear gradient from 50 mM to 800 mM NaCl in buffer A was formed. 21 ml fractions were collected. Fractions were assayed for PmeI restriction activity with lambda DNA and the midpoint of eluted activity was found to be at approximately 480 mM NaCl concentration. A total of 12 fractions were pooled and the amount of enzyme activity was estimated to be 750,000 units. This heparin-sepharose pool was applied to a 12 ml hydroxylapatite (HPT) column (Calbiochem; LaJolla, Calif.) equlibrated in buffer B (20 mM $KPO_4$, 6 mM 2-mercaptoethanol, 0.1 mM EDTA, 5% glycerol, pH 6.8) containing 50 mM NaCl (buffer B.05), washed with 36 ml of buffer B.05 and followed by a 120 ml linear gradient from 50 mM NaCl to 1 M NaCl in buffer B. 1.2 ml fractions were collected. Fractions were assayed for PmeI activity with lambda DNA. The midpoint of restriction enzyme activity eluted at approximately 500 mM NaCl. A total of 13 fractions were pooled and dialyzed against buffer C (20 mM $KPO_4$, 1 mM DTT, 0.1 mM EDTA, 5% glycerol, pH 6.8) contain 50 mM NaCl (buffer C.05) overnight. The dialyzed solution was applied to a 1 ml polyCat A column (Custom LC, Inc.; Houston, Tex.) equilibrated in buffer C.05, followed by a 50 ml linear gradient from 50 mM NaCl to 500 mM NaCl in buffer C. 1 ml fractions were collected and the fractions were assayed for restriction enzyme activity with lambda DNA. The PmeI activity eluted at approximately 270 mM NaCl. 3 fractions were pooled together, diluted with 5 volumes of buffer A and loaded onto a 1 ml Mono Q FPLC column (Pharmacia; Piscataway, N.J.) equilibrated with buffer A.05. The column was washed with 2 ml of buffer A.05 and the PmeI activity eluted with the flow through and the wash. PmeI containing fractions were pooled together and loaded directly onto a 3 ml Heparin-TSK FPLC column (TosoHaas; Philadelphia, Pa.) equilibrated with buffer A.05. The column was washed with 2 ml of buffer A.05 followed by a 60 ml linear gradient of 50 mM NaCl to 500 mM NaCl in buffer A. 1 ml fractions were collected and the PmeI activity was assayed with lambda DNA. The peak of restriction enzyme activity eluted at 300 mM NaCl. The amount of PmeI restriction enzyme activity purified was estimated to be 116,000 units. The peak fraction was loaded onto an SDS-PAGE protein gel and subjected to electrophoresis. The gel was stained with Coomassie blue R-250 and a prominent band at approximately 26 kD corresponding to the PmeI restriction endonuclease activity was observed.

3. Amino Terminal PmeI protein sequence: The PmeI restriction endonuclease, prepared as described in section 2 above, was subjected to electrophoresis and electroblotted according to the procedure of Matsudaira (Matsudaira, P., *J. Biol. Chem.* 262:10035–10038 (1987)), with modifications as previously described (Looney, et al., *Gene* 80:193–208 (1989)). The membrane was stained with Coomassie blue R-250 and the protein band of approximately 26 kD was excised and subjected to sequential degradation on an Applied BioSystems Division, Perkin-Elmer Corporation (Foster City, Calif.) Model 407A gas phase protein sequencer (Waite-Rees, et al., *J. Bacteriol.* 173:5207–5219 (1991)). The first 24 residues of the 27 kD protein corresponded to (Met)-Thr-Thr-Asn-Ser-Pro-Ser-Asp-Val-Gly-Met-Ile-Asp-Glu-Cys-Leu-Ser-Ile-Val-Xaa-Thr-Xaa-Leu-Ala (SEQ ID NO:4). 4. Amplification of N-terminal PmeI DNA: A portion of the PmeI endonuclease gene is amplified using degenerate DNA primers based on the amino acid sequence obtained in step 3. Two primers corresponding to the amino acid residues 1 through 6 (M)TTNSP (SEQ ID NO:1) are synthesized: PmeI-PS1 5' GTTGGATCCAT- GACNACNAAYTCNCC 3' (SEQ ID NO:5) and PmeI-PS2 5' GTTGGATCCATGACNACNAAYAGYCC 3' (SEQ ID NO:6). A primer corresponding to amino acid residues 10 through 14 MIDEC, PmeI-PS3 5' GTTCTGCAGRCAYT-CRTCDATCAT 3' (SEQ ID NO:7) is synthesized to hybridize at the reverse strand of DNA. A reaction mix was made by combining:

30 ul of 10×Vent® reaction buffer
18 ul of 4 mM dNTP solution
15 ul of primer PmeI-PS1
15 ul of primer PmeI-PS2
3 ul of *Pseudomonas mendocina* DNA (approximately 600 ng)
219 ul dH$_2$O
6 ul (12 units) of Vent® Exo$^-$ polymerase (NEB#257)

The mix was split into three 94 ul aliquots; to the first is added 6 ul of dH$_2$O, to the second is added 3 ul of dH$_2$O and 3 ul of 100 mM MgSO$_4$ (5 mM Mg$^{++}$ final concentration) and to the last is added 6 ul 100 mM MgSO$_4$ (8 mM Mg$^{++}$ final concentration). The PCR amplification conditions are: 95° C. for 2 minutes for one cycle, followed by 20 cycles of 95° C. for 30 seconds, 40° C. for 30 seconds and 72° C. for 5 seconds. The PCR amplified DNA is size selected on a 3.5% NuSieve agarose gel and cloned into pUC19. Individual clones of the amplified DNA are sequenced. Clones containing both PmeI-PS1 and PmeI-PS2 are observed, leaving the codon usage for amino acid five, serine, in question.

5. Cloning DNA adjacent to the N-terminal end of PmeI restriction endonuclease gene: Template preparation for inverse PCR amplification: 3 ug of *Pseudomonas mendocina* DNA was digested with 20 units of ApoI restriction endonuclease in 100 ul 1×NEBuffer #3 (50 mM Tris-HCl, 10 mM MgCl$_2$, 100 mM NaCl, 1 mM DTT, pH 7.9) for 1 hour at 50° C. The restriction digestion mixture was extracted with one volume of equilibrated phenol:chloroform (50:50, v/v) and the aqueous phase was recovered and extracted with one volume of chloroform two times. The DNA was precipitated by the addition of ⅒th volume of 5 M NaCl and 1 volume of 2-propanol and washed with 70% ice cold ethanol. The DNA was resuspended in 50 ul of 1×TE. 10 ul of this digested *Pseudomonas mendocina* DNA (approximately 0.5 ug) was circularized in 500 ul1×ligase buffer using 2000 U of T4 DNA ligase at 16° C. overnight. A portion of this circularization reaction was used as DNA template for subsequent inverse PCR reactions. Circularized BsaHI, BsrFI, BstYI, EaeI, HaeII, Sau3AI, NlaIII, EagI and BssHII digested *Pseudomonas mendocina* DNA were prepared in the same manner.

One forward or coding strand primer, PmeI-IP1 and two reverse or noncoding strand primers, PmeI-IP2 and PmeI-IP3 of sequences shown below were synthesized based on DNA sequences obtained from step 4. Primer PmeI-IP1 was designed to hybridize nucleotides corresponding to amino acid residues 8 to 13 Asp-Val-Gly-Met-Ile-Asp (SEQ ID NO:8) and the first nucleotide G of the codon coding for residue 14 Glu. A BamHI restriction site was also included in this primer to facilitate cloning. Primer PmeI-IP2 was designed to hybridize the last two nucleotides of the codon coding for residue 2 Thr, nucleotides corresponding to amino acid residues 3 to 7 Thr-Asn-Ser-Pro-Ser (SEQ ID NO:9) and the first nucleotide of the codon coding for residue 8 Asp. A PstI restriction site was also included in this primer to facilitate cloning.

Primer PmeI-IP1
5'-GTTGGATCCGACGTCGGCATGATCGACG-3' (SEQ ID NO:10)
Primer PmeI-IP2
5'-GTTCTGCAGCTGAGGGGCTGTTCGTTG-3' (SEQ ID NO:11)
Primer PmeI-IP3
5'-GTTCTGCAGCTGAGGGCGAATTCGTTG-3' (SEQ ID NO:12)

It is often convenient to directly insert PCR fragments into vectors previously cleaved by restriction enzymes that produce blunt ends such as SmaI. This requires that the PCR fragments to be inserted to have phosphate groups at the 5' ends. To this end, 15 ul of the DNA primer PmeI-IP1 (200 uM) was phosphorylated by 20 units of T4 polynucleotide kinase in 1×T4 polynucleotide kinase buffer (70 mM Tris-HCl, 10 mM MgCl$_2$, 5 mM dithiothreitol, pH 7.6) supplemented with 1 mM ATP in a 100 ul reaction volume at 37° C. for one hour. Primers PmeI-IP2 and PmeI-IP3 were also phosphorylated at the 5' end as described above. The T4 DNA polynucleotide kinase was heat inactivated by incubating at 65° C. for 20 minutes. The phosphorylated primers were diluted with 2 volumes of 1×TE to a final concentration of 10 uM and were used in the following PCR reactions.

Inverse PCR reactions were performed with digested, circularized *Pseudomonas mendocina* DNA as templates using the phosphorylated primers PmeI-IP1 and PmeI-IP2. Three different Mg$^{++}$ concentration was used in inverse PCR reactions against an individual DNA template. A reaction mix was made by combining:

30 ul of 10×Vent® reaction buffer
18 ul of 4 mM dNTP solution
15 ul of phosphorylated primer PmeI-IP1
15 ul of phosphorylated primer PmeI-IP2
36 ul of circularized DNA template (approximately 25 ng)
168 ul dH$_2$O
6 ul (12 units) of Vent® Exo$^-$ polymerase NEB#257

The mix was split into three 94 ul aliquots; to the first was added 6 ul of dH$_2$O, to the second was added 3 ul of dH$_2$O and 3 ul of 100 mM MgSO$_4$ (5 mM Mg$^{++}$ final concentration) and to the last was added 6 ul 100 mM MgSO$_4$ (8 mM Mg$^{++}$ final concentration). The PCR amplification conditions were: 95° C. for 2 minutes for one cycle, followed by 5 cycles of 95° C. for 30 seconds, 50° C. for 30 seconds and 72° C. for 2.5 minutes, followed by 20 cycles of 95° C. for 30 seconds, 65° C. for 30 seconds and 72° C. for 2.5 minutes. 15 ul of the PCR reaction was analyzed by electropheresis on a 0.8% agarose gel. Among some unspecific amplified DNA background, the following products were observed: a 1700 bp fragment and two closely spaced fragments around 1500 bp from ApoI digested circular template, a 1500 bp fragment from BstYI digested circular template, a 900 bp fragment and a 750 bp fragment from BsaHI digested circular template and a 2500 bp fragment from EagI digested circular template. These amplified product were gel purified. Gel purification: 100 ul of PCR reactions were electrophoresed into 1% LMP agarose, bands were excised from the gel, melted at 65° C. for five minutes, cooled to 40° C. for 5 minutes and the agarose was digested by the addition of 5 units of β-agarase (New England Biolabs #392) with incubation at 40° C. for 1 hour. It was then extracted with one volume of equilibrated phenol:chloroform (50:50, v/v) and the aqueous phase was recovered and extracted with one volume of chloroform two times. The DNA was precipitated by the addition of ⅒ volume of 5 M NaCl and 2 volumes of 2-propanol, washed with 70% ethanol, air dried and resuspended in 50 ul of 1× TE buffer.

Inverse PCR reactions were also performed with phosphorylated primers PmeI-IP1 and PmeI-IP3 using the same set of templates in the similar manner as described above. 15 ul of the PCR reaction was analyzed by electropheresis on a 0.8% agarose gel. The following fragments were gel purified: a 2000 bp, a 1800 bp and a 870 bp fragments from ApoI digested circular template, a1350 bp fragment from BstYI digested circular template, a 1200 bp fragment BsrFI digested circular template, a 2100 bp and a1400 bp fragments from BssHII digested circular template, a 2500 bp fragment from EagI digested circular template, and a 800 bp fragment from NlaIII digested circular template.

Each of the gel purified amplified DNA product was ligated into the vector pUC19 respectively as follows: 5 ul of gel purified DNA was ligated to 100 ng of pUC19 vector previously cleaved with SmaI and dephosphorylated with Calf Intestinal Alkaline Phosphatase (CIP) in a final volume of 20 ul in 1×T4 DNA ligase buffer (50 mM Tris-HCl, 10 mM $MgCl_2$, 10 mM DTT, 1 mM ATP, 25 ug/ml BSA, pH 7.5) with 400 U T4 DNA ligase. 10 ul of the ligation mixture was then transformed into *E. coli* strain ER2267 and plated on L-broth plates containing 100 ug/ml ampicillin, 40 ug/ml Xgal and 50 ug/ml IPTG for individual colonies. White colonies were individually picked to inoculate 10 ml of L-broth containing 100 ug/ml ampicillin and were allowed to propagate at 37° C. overnight. Clones of the desired construct were identified by performing minipreps, digesting the purified DNA and analyzing it by agarose gel electrophoresis.

Miniprep Procedure: Each culture was centrifuged at 8000 rpm for 5 minutes; the supernatant was discarded and the cell pellet was resuspended in 1.0 ml of 25 mM Tris, 10 mM EDTA, 50 mM glucose, pH 8.0. After 10 minutes at room temperature, 2 ml of 0.2 M NaOH, 1% SDS was added to each tube and the tubes were shaken to lyse the cells and then placed on ice. Once the solutions had cleared, 1.5 ml of 3 M sodium acetate pH 4.8, was added to each and shaken. The precipitates that formed were spun down at 15,000 rpm, 4° C. for 10 minutes. Each supernatant was poured and mixed. After 10 minutes at room temperature, the tubes were spun at 15,000 rpm for 10 minutes to pellet the precipitated nucleic acids. The supernatants were discarded and the pellets were air-dried at room temperature for 30 minutes. Once dry, the pellets were dissolved in 850 ul of 10 mM Tris pH 8.0, 1 mM EDTA, containing 100 ug/ml RNase and incubated for 1 hour at 37° C. to digest the RNA. The DNA was precipitated by the addition of 85 ul of 5 M NaCl followed by 600 ul of isopropanol. After 10 minutes at room temperature the DNA was spun down by centrifugation for 5 minutes, the supernatants were discarded, the pellets were dried and then redissolved in a final solution of 150 ul of 10 mM Tris, 1 mM EDTA pH 8.0 (1×TE). The plasmid minipreps were subsequently analyzed by digestion with various restriction endonucleases.

6. DNA Sequencing: DNA sequencing was performed using an ABI 373 automated sequencing system according to the manufacturer's instructions, using M13/pUC primers #1233 and #1224 (NEB). Miniprep DNA preparations of various pUC19 constructs containing DNA fragments from inverse PCR reactions described in section 5 were used as templates. Only one clone had sequence matching the PmeI endonuclease amino acid sequence; a 1400 bp fragment amplified from BssHII digested circular template in a inverse PCR reaction using primers PmeI-IP1 and PmeI-IP3. This clone was designated as pUC19BssHII21. The DNA sequence at one end of this clone matched with the portion of the PmeI endonuclease sequence 3' from the primer PmeI-IP1. However, the DNA sequence from the other end did not match the portion of the PmeI endonuclease sequence 3' from the primer PmeI-IP3. It was concluded that primer PmeI-IP1 hybridized at the desired position on PmeI genomic DNA and primer PmeI-IP3 hybridized elsewhere on the PmeI genomic DNA, likely due to mismatches on the primer sequence. Since there were discrepancies in the codon sequences for fourth and fifth residues, Asn and Ser, a new set of inverse PCR primers was designed to exclude DNA sequences coding for these residues.

7. Inverse PCR amplifications using new set of primers to amplify and clone DNA adjacent to N-terminus of the endonuclease gene: Primers PmeI-IP4 and PmeI-IP5 were designed according to the DNA sequences obtained in step 6. Primer PmeI-IP4 included nucleotides corresponding to amino acid residues Val-Gly-Met-Ile-Asp (SEQ ID NO:13) and the first two nucleotides of the codon for Glu. A BamHI site was also included in this primer to facilitate cloning.

Primer PmeI-IP4
5'-GTTGGATCCGTCGGCATGATCGACGA-3' (SEQ ID NO:14)

Primer PmeI-IP5 was designed to hybridize with the first two nucleotides of codon for Gly and nucleotides corresponding to amino acid residues Val-Asp-Ser-Pro. A BamHI site was also included in this primer to facilitate cloning.

Primer PmeI-IP5
5'-CATGGATCCGACGTCTGAGGG-3' (SEQ ID NO:15)

Inverse PCR reactions were carried out using BsaWI digested, circularized PmeI DNA as the template. In the reaction that was successful in amplifying the product, a reaction mix was made by combining:
ul of 10×Vent® reaction buffer
6 ul of 4 mM dNTP solution
3 ul of 100 mM $MgSO_4$ (5 mM Mg++ final concentration)
5 ul of phosphorylated primer PmeI-IP4
5 ul of phosphorylated primer PmeI-IP5
12 ul of circularized DNA template (approximately 25 ng)
58 ul $dH_2O$
2 ul (4 units) of Vent® Exo⁻ polymerase NEB#257

The PCR amplification conditions were: 95° C. for 2 minutes for one cycle, followed by 5 cycles of 95° C. for 30 seconds, 40° C. for 1 minute and 72° C. for 2.5 minutes, followed by cycles of 95° C. for 30 seconds, 60° C. for 1 minute and 72° C. for 2.5 minutes. 15 ul of the PCR reaction was analyzed by electrophoresis on a 0.8% agarose gel.

A 900 bp product was observed, gel purified and resuspended in 50 ul of 1×TE. 5 ul of this DNA was digested with 20 U of BamHI (NEB#136) in a final volume of 20 ul in 1×BamHI Buffer (150 mM NaCl, 10 mM Tris-HCl, 10 mM $MgCl_2$, 1 mM dithiothreitol, pH 7.9)) at 37° C. for 1 hour. The restriction endonuclease BamHI was heat inactivated by incubating the reaction mixture at 78° C. for 20 minutes. 5 ul of the digested DNA was ligated to 100 ng of the vector pUC19 previously cleaved with BamHI, dephosphorylated with CIP and agarose gel purified, using 400 U of T4 DNA ligase in 20 ul final volume of 1×T4 DNA ligase buffer at 16° C. for 2 hours. 10 ul of the ligation mixture was transformed into *E. coli* strain ER2267 and plated on L-broth plates containing 100 ug/ml ampicillin, 40 ug/ml Xgal and 50 ug/ml IPTG for individual colonies. White colonies were individually picked to inoculate 10 ml of L-broth containing 100 ug/ml ampicillin and were allowed to propagate at 37° C. overnight. Clones of the desired construct were identified by performing minipreps, digesting the purified DNA and analyzing it by agarose gel electrophoresis. One clone, designated as pUC19BsaWI5, containing the 900 bp fragment was sequenced.

8. DNA sequencing of the clone pUC19BsaWI5: DNA sequencing was performed using an ABI 373 automated sequencing system according to the manufacturer's instructions, using M13/pUC primers #1233 and #1224 (New England Biolabs, Beverly, Mass.) and miniprep DNA preparation of pUC19BsaWI5 as template. The DNA sequence at one end of this clone matched with the portion of the PmeI endonuclease sequence corresponding to and 3' from the primer PmeI-IP4. The DNA sequence from the other end also matched the portion of the PmeI endonuclease sequence corresponding to and 3' from the primer PmeI-IP5. The codon sequences for residues 4 (Asn) and 5 (Ser) were found to be 5' AAC 3' and 5' TCC 3'. An open reading frame of 693 bp with its N-terminal amino acid sequence matching the N-terminal protein sequence data obtained in section 3 was identified as the PmeI restriction endonuclease gene. The six frame amino acid sequence translated from the 700 bp DNA sequence immediately 3' to the endonuclease gene were compared to the conserved amino acid motifs of various types of known methylases and no amino acid sequences homologous to these motifs could be identified. Similarly, no obvious methylase motifs could be found from the six frame amino acid sequence translated from the 200 bp DNA sequence immediately 5' adjacent to the endonuclease gene. In order to locate a possible PmeI methylase gene, DNA region located further away from both sides of the endonuclease gene was amplified, cloned and sequenced in the subsequent steps.

9. Cloning DNA 5' to the PmeI endonuclease gene: The following restriction endonuclease digested, circularized *Pseudomonas mendocina* DNA from section 5 were used as templates for inverse PCR amplification: ApoI, EagI, BssHII, BsrF, HaeII and BstYI. Primers PmeI-IP6 and PmeI-IP7 shown below were designed to anneal within and toward the 5' end of the PmeI endonuclease gene. Both primers contain a PstI site to facilitate cloning.

Primer PmeI-IP6
5'-phospho-GTTCTGCAGCTCGTTGTCTTCTTCTGC-3' (SEQ ID NO:16)

Primer PmeI-IP7
5'-phospho-ATCCTGCAGGCGACGTTCGGACGATG-3' (SEQ ID NO:17)

In the reaction that was successful in amplifying the product, a reaction mix was made by combining: 10 ul of 10×Vent® reaction buffer (containing 2 mM Mg$^{++}$ final concentration)
6 ul of 4 mM dNTP solution
5 ul of phosphorylated primer PmeI-IP6
5 ul of phosphorylated primer PmeI-IP7
12 ul of circularized DNA template (approximately 25 ng)
58 ul dH$_2$O
2 ul (4 units) of Vent® Exo$^-$ polymerase NEB#257

The PCR amplification conditions were: 95° C. for 2 minutes for one cycle, followed by 5 cycles of 95° C. for 20 seconds, 50° C. for 1 minute and 72° C. for 2.5 minutes, followed by 20 cycles of 95° C. for 30 seconds, 65° C. for 1 minute and 72° C. for 2.5 minutes. 15 ul of the PCR reaction was analyzed by electrophoresis on a 0.8% agarose gel.

Among some nonspecific amplified background DNA, a 1.8 kb product was observed in the ApoI circular template PCR reaction; a 1.6 kb product was observed in the BssHII circular template PCR reaction; a 3.3 kb product was observed in the BstYI circular template PCR reaction; a 1.6 kb product was observed in the EagI circular template PCR reaction, and a 0.9 kb product was observed in the HaeII circular template PCR reaction. These five products were gel purified and resuspended in 60 ul of 1×TE (BstYI product was resuspended in 20 ul of 1×TE). 5 ul of gel purified ApoI product was ligated to 100 ng of the vector pUC19 previously cleaved with SmaI, dephosphorylated with CIP and agarose gel purified, using 400 U of T4 DNA ligase in 20 ul final volume of 1×T4 DNA ligase buffer at 16° C. for 2 hours. The gel purified BssHII, EagI, HaeII and BstYI products were similarly ligated into pUC19 as described above. 10 ul of each ligation mixture was transformed into *E. coli* strain ER2267 and plated on L-broth plates containing 100 ug/ml ampicillin, 40 ug/ml Xgal and 50 ug/ml IPTG for individual colonies. White colonies were individually picked to inoculate 10 ml of L-broth containing 100 ug/ml ampicillin and were allowed to propagate at 37° C. overnight. Clones of the desired construct were identified by performing minipreps, digesting the purified DNA and analyzing it by agarose gel electrophoresis.

10. Sequencing DNA 5' to the endonuclease gene: The constructs with desired inserts from section 9 were sequenced with M13/pUC primers #1233 and #1224 (NEB) using an ABI 373 automated sequencing system according to the manufacturer's instructions. Miniprep DNA preparations of the constructs were used as templates. The ends of the 3.3 kb amplified product from the BstYI circularized template and the 0.9 kb amplified product from the HaeII circularized template matched with the known DNA region 3' to both inverse PCR primers PmeI-IP6 and PmeI-IP7. The complete sequence was obtained by primer walking and sequencing. The 3.3 kb product contained 2.9 kb new DNA sequence and the 0.9 kb product contained 200 bp new DNA sequence. No obvious methylase motifs were observed in the new DNA sequence.

11. Amplifying and cloning DNA 3' to the endonuclease gene: Two consecutive inverse PCR amplification experiments were performed to obtain DNA information 3' to the endonuclease gene.

A. Inverse PCR amplification #1: Template preparation for inverse PCR amplification: 3 ug of genomic *Pseudomonas mendocina* DNA was digested with 100 U of AatII restriction endonuclease in 1×NEBuffer #4 (20 mM Tris-acetate, 10 mM magnesium acetate, 50 mM potassium acetate, 1 mM DTT, pH 7.9) in 100 ul reaction volume for 1 hour at 37° C. The restriction digestion mixture was extracted with one volume of equilibrated phenol:chloroform (50:50, v/v) and the aqueous phase was recovered and extracted with one volume of chloroform two times. The DNA was precipitated by the addition of 1/10th volume of 5 M NaCl and 1 volume of 2-propanol and then washed with 70% ice cold ethanol. The DNA was resuspended in 50 ul of 1×TE. 10 ul of this digested *Pseudomonas mendocina* DNA (approximately 0.5 ug) was circularized in 500 ul1×ligase buffer using 2000 U of T4 DNA ligase at 16° C. overnight. Circularized HinpII, MscI, MseI, SacI, StuI and Tsp509I digested *Pseudomonas mendocina* DNA were prepared in the same manner. These circularized DNA as well as the BsaHI digested, circularized DNA from section 5 were used as templates for subsequent inverse PCR reactions.

Primers PmeI-IP8 and PmeI-IP9 of sequences shown below were used to amplify DNA 3' to the endonuclease gene. Both primers contain a PstI sites to facilitate cloning.

Primer PmeI-IP8
5'-pGGTCTGCAGTCGGGCAGAACGTGATATTCGA-3' (SEQ ID NO:18)

Primer PmeI-IP9
5'-pGTTCTGCAGGCCATTTGGCACCCTG-3' (SEQ ID NO:19)

In a reaction that was successful in amplifying the product, a reaction mix was made by combining:
10 ul of 10×Vent® reaction buffer (containing 2 mM Mg++ final concentration)
6 ul of 4 mM dNTP solution
5 ul of phosphorylated primer PmeI-IP8
5 ul of phosphorylated primer PmeI-IP9
12 ul of circularized DNA template (approximately 25 ng)
58 ul dH$_2$O
2 ul (4 units) of Vent® Exo⁻ polymerase NEB#257

The PCR amplification conditions were: 95° C. for 2 minutes for one cycle, followed by 5 cycles of 95° C. for 20 seconds, 52° C. for 30 seconds and 72° C. for 2.5 minutes, followed by 20 cycles of 95° C. for 30 seconds, 65° C. for 30 seconds and 72° C. for 2.5 minutes. 15 ul of the PCR reaction was analyzed by electrophoresis on a 0.8% agarose gel.

Among some non-specific amplified background DNA, a 1.1 kb product was observed in the AatII circular template PCR reaction, a 1.4 kb product was observed in the MscI circular template PCR reaction and a 0.7 kb product was observed in the BsaHI circular template PCR reaction. These products were gel purified and resuspended in 20 ul of 1×TE. 2 ul of gel purified AatII product was ligated to 100 ng of the vector pUC19 previously cleaved with SmaI, dephosphorylated with CIP and agarose gel purified, using 400 U of T4 DNA ligase in 20 ul final volume of 1×T4 DNA ligase buffer at 16° C. for 2 hours. The gel purified MscI and BsaHI products were similarly ligated into pUC19 as described above. 10 ul of each ligation mixture was transformed into *E. coli* strain ER2267 and plated on L-broth plates containing 100 ug/ml ampicillin 40 ug/ml Xgal and 50 ug/ml IPTG for individual colonies. White colonies were individually picked to inoculate 10 ml of L-broth containing 100 ug/ml ampicillin and were allowed to propagate at 37° C. overnight with agitation and aeration. Clones of the desired construct were identified by performing minipreps, digesting the purified DNA and analyzing it by agarose gel electrophoresis. The amplified products in these clones were sequenced using M13/pUC primers #1233 and #1224 (NEB). The newly obtained DNA sequence was used to design primers PmeI-IP10 and PmeI-IP11 shown below in a subsequent inverse PCR amplification to obtain more DNA sequence information 3' to this region.
PmeI-IP10
5'-phosho-GTTCTGCAGCCGTTTCGATGGGCCTTCTC-3' (SEQ ID NO:20)

PmeI-IP11
5'-phospho-GTTCTGCAGAATGAGCTGCGCCAGTTG-3' (SEQ ID NO:21)

B. Inverse PCR amplification #2: HaeII digested and circularized *Pseudomonas mendocina* DNA (section 5) was used as template in this inverse PCR amplification with primers PmeI-IP10 and PmeI-IP11. In a reaction that was successful in amplifying the product, a reaction mix was made by combining:

10 ul of 10×Vent® reaction buffer (containing 2 mM Mg++ final concentration)
6 ul of 4 mM dNTP solution
5 ul of phosphorylated primer PmeI-IP10
5 ul of phosphorylated primer PmeI-IP11
12 ul of circularized DNA template (approximately 25 ng)
58 ul dH$_2$O
2 ul (4 units) of Vent® Exo⁻ polymerase NEB#257

The PCR amplification conditions were: 95° C. for 2 minutes for one cycle, followed by 5 cycles of 95° C. for 20 seconds, 6° C. for 30 seconds and 72° C. for 2.5 minutes, followed by 20 cycles of 95° C. for 30 seconds, 65° C. for 30 seconds and 72° C. for 2.5 minutes. 15 ul of the PCR reaction was analyzed by electrophoresis on a 0.8% agarose gel. A 0.7 kb amplified product was obtained and cloned into pUC19 vector previously cleaved by SmaI, dephosphorylated with CIP and agarose gel purified. Minipreps were performed to identify plasmid clones carrying the desired inserts. The 0.7 kb product was sequenced using M13/pUC primers #1233 and #1224 (NEB). Approximately 1.57 kb DNA sequence was obtained 3' to the endonuclease gene and no obvious methylase motifs could be found from the six frame amino acid translation of this DNA.

12. Expressing DraI methylase in vector pNEB193 to determine if DNA modified by DraI methylase can be protected from PmeI restriction digestion: A DraI methylase producing clone, pDraIRM9.7-G2, containing the DraI methylase gene on a 5.5 kb insert in vector pBR322 (Jack Benner, New England Biolabs,Inc.) was partially digested with Sau3AI as follows: 7 ug of pDraIRM9.7-G2 DNA was diluted into 350 ul of 1×Sau3AI buffer (100 mM NaCl, 10 mM Bis Tris Propane-HCl, 10 mM MgCl$_2$, 1 mM DTT, pH 7.0). This mixture was used to prepare a serial dilution of Sau3AI restriction endonuclease from 1 unit/ug DNA to ¹⁄₆₄ unit/ug DNA by a factor of two each dilution in a final volume of 50 ul. These reactions were incubated at 37° C. for 15 minutes and the Sau3AI restriction endonuclease was subsequently heat-killed at 68° C. for 20 minutes. 0.5 ug of the digested DNA produced from digestion of ⅛ unit of Sau3AI per ug of DNA was used to ligate to 200 ug of pNEB193 vector previously cleaved with BamHI and dephosphorylated with CIP in 40 ul 1×T4 DNA ligase buffer containing 800 U of T4 DNA ligase for 16 hours at 16° C. The ligation mixture was transformed into 200 ul of *E. coli* strain ER2426 competent cells and plated on L-broth plates containing 100 ug/ml ampicillin. Approximately 10,000 colonies were obtained, and these were scraped into 6 ml of mM Tris, 10 mM MgCl$_2$, pH 7.5. 2 ml of this pool was inoculated into 100 ml of L-broth containing 100 ug/ml ampicillin and allowed to grow at 37° C. with shaking for 8 hours. Plasmids were isolated using a 1× scale-up of the miniprep procedure as described in section 5 above. The miniprep DNA was resuspended into 500 ul of 1×TE and 2 ul was digested with 40 units of DraI in 50 ul of 1×NEBuffer 4 at 37° C. for 2 hours. 10 ul of the digestion mixture was transformed into 50 ul of *E. coli* strain ER 2426 competent cells and plated on L-broth plates containing 100 ug/ml ampicillin. Plasmids from 9 individual transformants were isolated by miniprep procedure and digested with DraI restriction endonuclease. Eight clones were fully protected from DraI digestion. These were subsequently digested with PmeI restriction endonuclease and were fully protected from PmeI restriction digestion as well.

13. Overexpressing the PmeI endonuclease:
A. Cloning the DraI methylase on a compatible vector: The DraI methylase gene was expressed by inserting the gene into the BamHI site of pACYC184. To accomplish this, 0.5 ug of the Sau3AI partially digested pDraIRM9.7-G2 DNA prepared in section 12 was ligated into vector pACYAC184, previously cleaved with BamHI and dephosphorylated, in 40 ul of 1×T4 DNA ligase buffer containing 800 U of T4 DNA ligase for 2 hours at 16° C. The ligation mixture was transformed into 200 ul of *E. coli* strain ER2426 competent cells and plated on L-broth plates containing 25 ug/ml chloramphenicol. Approximately 1,600 colonies were obtained and these were scraped into 4 ml of 10 mM Tris, 10 mM MgCl$_2$, pH 7.5. 1 ml of this pool was inoculated into 75 ml of L-broth containing 25 ug/ml chloramphenicol and allowed to grow at 37° C. with shaking for 8 hours. Plasmids were isolated using a 10× scale-up of the miniprep procedure as described in section 5 above. The miniprep DNA was resuspended into 500 ul of 1×TE and centrifuged at 14,000 rpm for minutes. 336 ul of the cleared supernatant was mixed with 64 ul of 5 M NaCl and 400 ul of 13% PEG 8000 and incubated on ice for 1 hour. The DNA was spun down at 14,000 rpm at 4° C. for 5 minutes, washed with ice cold 70% ethanol and air dried. The DNA pellet was resuspended in 500 ul of 1×TE and 5 ul of it was digested with 60 units of DraI in 50 ul of 1×NEBuffer 4 at 37° C. for 1 hour. 5 ul of this DraI digested DNA was transformed into 50 ul of ER2426 competent cells and plated on L-broth plates containing 25 ug/ml chloramphenicol to obtain individual transformants. Plasmids from 14 individual transformants were isolated by miniprep procedure and digested with DraI restriction endonuclease, and of these twelve clones were fully protected from DraI digestion. Further restriction analysis showed that two clones, pACYC184DraIM10 and pACYC184DraI M13, were identical and contained the smallest insert fragment of approximately 3 kb. Clone pACYC184DraIM10 was used for PmeI endonuclease expression.

B. Endonuclease cloning: The restriction endonuclease gene was expressed by inserting the gene into an expression vector, pRRS, directly downstream of a strong inducible promoter (PlacUV5) and a strongly recognized ribosome binding site. To accomplish this, two oligonucleotide primers were made utilizing the DNA sequence data. The forward oligonucleotide primer contained a PstI site to facilitate cloning, a stop codon in frame with the lacZ gene to terminate translation of the lacZ protein, a strongly recognized ribosome binding site, seven nucleotide spacer between the rbs and the ATG start codon of the PmeI endonuclease gene and 24 nucleotides complementary to *Pseudomonas mendocina* DNA for hybridization:

Primer PmeIRexp1:
5'-GAGACTGCAGGAGGTAATTCATATGACCACAAA-CTCCCCCTCA GAC-3' (SEQ ID NO:22)

The reverse primer was designed to hybridize to *Pseudomonas mendocina* DNA 84 bp 3' to the 3' end of the PmeI endonuclease gene. It contained a BglII site and a SalI restriction site to facilitate cloning and 21 nucleotides complementary to *Pseudomonas mendocina* DNA for hybridization:

Primer PmeIRexp2:
5'-CAAGAGATCTAGTCGACCGGTGTTAGCAA-CCCGATAC-3' (SEQ ID NO:23)

These two primers were used to amplify the PmeI endonuclease gene from *Pseudomonas mendocina* genomic DNA by combining:

10 ul 10×Vent® reaction buffer
6 ul of 4 mM dNTPs
2 ul (400 ng) *Pseudomonas mendocina* genomic DNA
5 ul (uM stock) primer PmeIRexp1
5 ul (uM stock) primer PmeIRexp2
4 ul of 100 mM MgSO$_4$
66 ul dH$_2$O
0.6 ul (1.2 units) Vent® polymerase (2 unit/ul stock)

and amplifying at 95° C. for 3 minutes for 1 cycle, followed by 4 cycles of 95° C. for 30 seconds, 60° C. for 20 seconds, 72° C. for 50 seconds, followed by 20 cycles of 95° C. for 30 seconds, 65° C. for 20 seconds and 72° C. for 50 seconds. The amplification product of approximately 850 bp was gel purified, cleaved with BglII and PstI, phenol-chloroform extracted, precipitated, resuspended in TE and ligated into pRRS vector previously cleaved with PstI and BamHI and gel purified. The ligation reaction was transformed into *E. coli* strain ER2426 carrying the DraI methylase gene construct pACYC184DraIM10 and plated on L-broth plates containing 25 ug/ml chloramphenicol and 100 ug/ml of ampicillin for individual transformants. Seven individual transformants were inoculated into 10 ml of L-broth containing 25 ug/ml chloramphenicol and 100 ug/ml ampicillin, grown at 37° C. with shaking to mid-log phase and induced with 0.5 mM IPTG for 16 hours. The cell pellets were spun down at 5000 rpm for 5 minutes at 4° C., resuspended in 1.5 ml of 20 mM Tris, 0.1 mM EDTA, 1 mM DTT, 50 mM NaCl, pH 7.5 and sonicated. The extracts were used to digest lambda DNA in 50 ul 1×NEBuffer #2 (10 mM Tris, 10 mM MgCl$_2$, 50 mM NaCl, 1mM DTT, pH7.9)) at 37° C. for 30 minutes. All clones expressed PmeI endonuclease activity. One of these clones, designated as pRRSPmeIR1/pACYC184DraIM10, was selected for producing the PmeI endonuclease and given the strain designation of NEB #1081. A titration of the PmeI restriction endonuclease activity produced from crude extracts of NEB #1081 is shown in FIG. 1. The enzyme titer was approximately 1×10$^7$ units/g of cells.

14. The PmeI restriction endonuclease may be produced from NEB #1081 by propagation to mid-log phase in a fermenter containing L-broth medium with ampicillin (100 ug/ml) and chloramphenicol (25 ug/ml). The culture is induced by the addition of IPTG to a final concentration of 0.3 mM and allowed to continue growing for 16 hours. The cells are harvested by centrifugation and may be stored at −70° C. or used immediately.

15. Purification of the PmeI restriction endonuclease from NEB #1081 can be accomplished by a combination of standard protein purification techniques, such as affinity-chromatography or ion-exchange chromatography, as outlined in step 2 above. The PmeI restriction endonuclease obtained from this purification is substantially pure and free of non-specific endonuclease and exonuclease contamination.

A sample of the *E. coli* containing both pRRSPmeIR1 and pACYC184DraIM10 (NEB#1081) has been deposited under the terms and conditions of the Budapest Treaty with the American Type Culture Collection on Nov. 25, 1997 and received ATCC Accession Number 98596.

What is claimed is:

1. Isolated DNA coding for the PmeI restriction endonuclease, wherein the isolated DNA is obtainable from *Pseudomonas mendocina*.

2. A recombinant DNA vector comprising a vector into which a DNA segment coding for the PmeI restriction endonuclease has been inserted.

3. Isolated DNA coding for the PmeI restriction endonuclease and methylase, wherein the isolated DNA is obtainable from ATCC No. 98596.

4. A cloning vector which comprises the isolated DNA of claim 3.

5. The cloning vector of claim 4, wherein the cloning vector comprises both pRRSPmeIR1 and pACYC184DraIM10.

6. A host cell transformed by the cloning vector of claim 2, 4, or 5.

7. A method of producing a PmeI restriction endonuclease comprising culturing a host cell transformed with the vector of claim 2, 4, or 5 under conditions suitable for expression of said endonuclease.

* * * * *

UNITED STATES PATENT AND TRADEMARK OFFICE
CERTIFICATE OF CORRECTION

PATENT NO. : 5,945,288

DATED : August 31, 1999

INVENTOR(S) : Zhiyuh Chang and Richard D. Morgan,

It is certified that error appears in the above-identified patent and that said Letters Patent is hereby corrected as shown below:

| | |
|---|---|
| Column 1, line 5 | after "relates" insert --to-- |
| Column 2, line 40 | replace "258:235" with --258:1235-- |
| Column 8, line 6 | replace "71:342" with --71:1342-- |
| Column 13, line 8 | delete "a" second & third occurrence |
| Column 13, line 8 | replace "fragments" with --fragment-- |
| Column 13, line 10 | after "fragment" insert --from-- |
| Column 13, lines 11-12 | replace "fragments" with --fragment-- |
| Column 13, line 13 | replace "a" with --an-- |
| Column 13, line 65 | replace "a" with --an-- |
| Column 16, line 67 | after "contain" delete "a" |
| Column 1, line 33 | replace "TTAAA" with --TTTAAA-- |
| Column 3, line 46 | replace "GTTAAAC" with --GTTTAAAC-- |
| Column 5, line 36 | replace "pAI117" with --pAII17-- |
| Column 7, line 2 | after "as" delete "Proc. Natl. Acad." |
| Column 9, line 52 | after "600 ml" delete "10" |
| Column 14, line 38 | before "ul" insert --10-- |
| Column 18, line 12 | replace "6°" with --60°-- |
| Column 18, line 31 | replace "Sau3A1" with --Sau3AI-- |

UNITED STATES PATENT AND TRADEMARK OFFICE
CERTIFICATE OF CORRECTION

PATENT NO. : 5,945,288

DATED : August 31, 1999

INVENTOR(S) :
    Zhiyuh Chang and Richard D. Morgan,

It is certified that error appears in the above-identified patent and that said Letters Patent is hereby corrected as shown below:

Column 18, line 48    after "of" insert --10--
Column 18, line 52    replace "1X" with --10X--
Column 20, line 4     before "uM" insert --10--
Column 20, line 5     before "uM" insert --10--

Signed and Sealed this

Second Day of May, 2000

Attest:

Q. TODD DICKINSON

Attesting Officer    Director of Patents and Trademarks

SEQUENCE LISTING (1) GENERAL INFORMATION:

(iii) NUMBER OF SEQUENCES: 23

(2) INFORMATION FOR SEQ ID NO:1:

(i) SEQUENCE CHARACTERISTICS:
       (A) LENGTH: 6 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO:1:

Met Thr Thr Asn Ser Pro
1               5

(2) INFORMATION FOR SEQ ID NO:2:

(i) SEQUENCE CHARACTERISTICS:
       (A) LENGTH: 5 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO:2:

Met Ile Asp Glu Cys
1               5

(2) INFORMATION FOR SEQ ID NO:3:

(i) SEQUENCE CHARACTERISTICS:
       (A) LENGTH: 6 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO:3:

Asp Val Gly Met Ile Asp
1               5

(2) INFORMATION FOR SEQ ID NO:4:

(i) SEQUENCE CHARACTERISTICS:
       (A) LENGTH: 24 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO:4:

Met Thr Thr Asn Ser Pro Ser Asp Val Gly Met Ile Asp Glu Cys Leu
1               5                   10                  15

Ser Ile Val Xaa Thr Xaa Leu Ala
            20

(2) INFORMATION FOR SEQ ID NO:5:

(i) SEQUENCE CHARACTERISTICS:
       (A) LENGTH: 26 base pairs
       (B) TYPE: nucleic acid

```
        (C) STRANDEDNESS: single
        (D) TOPOLOGY: linear (ii) MOLECULE TYPE: Genomic DNA (ix) FEATURE:
        (A) NAME/KEY: Other
        (B) LOCATION: 15...15
        (D) OTHER INFORMATION: N=G, A, C, or T(U)

(ix) FEATURE:
        (A) NAME/KEY: Other
        (B) LOCATION: 18...18
        (D) OTHER INFORMATION: N=G, A, C, or T(U)

(ix) FEATURE:
        (A) NAME/KEY: Other
        (B) LOCATION: 21...21
        (D) OTHER INFORMATION: Y=C or T(U)

(ix) FEATURE:
        (A) NAME/KEY: Other
        (B) LOCATION: 24...24
        (D) OTHER INFORMATION: N=G, A, C, or T(U)

(xi) SEQUENCE DESCRIPTION: SEQ ID NO:5:

GTTGGATCCA TGACNACNAA YTCNCC                                        26

(2) INFORMATION FOR SEQ ID NO:6:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: Genomic DNA (ix) FEATURE:
        (A) NAME/KEY: Other
        (B) LOCATION: 15...15
        (D) OTHER INFORMATION: N=G, A, C, or T(U)

(ix) FEATURE:
        (A) NAME/KEY: Other
        (B) LOCATION: 18...18
        (D) OTHER INFORMATION: N = G, A, C, or T(U)

(ix) FEATURE:
        (A) NAME/KEY: Other
        (B) LOCATION: 21...21
        (D) OTHER INFORMATION: Y = C or T(U)

(ix) FEATURE:
        (A) NAME/KEY: Other
        (B) LOCATION: 24...24
        (D) OTHER INFORMATION: Y = C or T(U)

(xi) SEQUENCE DESCRIPTION: SEQ ID NO:6:

GTTGGATCCA TGACNACNAA YAGYCC                                        26

(2) INFORMATION FOR SEQ ID NO:7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: Genomic DNA (ix) FEATURE:
        (A) NAME/KEY: Other
        (B) LOCATION: 10...10
        (D) OTHER INFORMATION: R = A or G
```

(ix) FEATURE:
            (A) NAME/KEY: Other
            (B) LOCATION: 13...13
            (D) OTHER INFORMATION: Y = C or T(U)

(ix) FEATURE:
            (A) NAME/KEY: Other
            (B) LOCATION: 16...16
            (D) OTHER INFORMATION: R = A or G (ix) FEATURE:
            (A) NAME/KEY: Other
            (B) LOCATION: 19...19
            (D) OTHER INFORMATION: D = G or A or T(U)

(xi) SEQUENCE DESCRIPTION: SEQ ID NO:7:

GTTCTGCAGR CAYTCRTCDA TCAT                                                  24

(2) INFORMATION FOR SEQ ID NO:8:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:8:

Asp Val Gly Met Ile Asp
1               5

(2) INFORMATION FOR SEQ ID NO:9:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:9:

Thr Asn Ser Pro Ser
1               5

(2) INFORMATION FOR SEQ ID NO:10:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: Genomic DNA (xi) SEQUENCE DESCRIPTION: SEQ ID NO:10:

GTTGGATCCG ACGTCGGCAT GATCGACG                                              28

(2) INFORMATION FOR SEQ ID NO:11:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: Genomic RNA (xi) SEQUENCE DESCRIPTION: SEQ ID NO:11:

GTTCTGCAGC TGAGGGGCTG TTCGTTG                                               27

(2) INFORMATION FOR SEQ ID NO:12:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:12:

```
GTTCTGCAGC TGAGGGCGAA TTCGTTG                                    27
```

(2) INFORMATION FOR SEQ ID NO:13:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:13:

```
Val Gly Met Ile Asp
 1               5
```

(2) INFORMATION FOR SEQ ID NO:14:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:14:

```
GTTGGATCCG TCGGCATGAT CGACGA                                     26
```

(2) INFORMATION FOR SEQ ID NO:15:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:15:

```
CATGGATCCG ACGTCTGAGG G                                          21
```

(2) INFORMATION FOR SEQ ID NO:16:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:16:

```
GTTCTGCAGC TCGTTGTCTT CTTCTGC                                    27
```

(2) INFORMATION FOR SEQ ID NO:17:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:17:

ATCCTGCAGG CGACGTTCGG ACGATG                                        26

(2) INFORMATION FOR SEQ ID NO:18:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:18:

GGTCTGCAGT CGGGCAGAAC GTGATATTCG A                                  31

(2) INFORMATION FOR SEQ ID NO:19:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:19:

GTTCTGCAGG CCATTTGGCA CCCTG                                         25

(2) INFORMATION FOR SEQ ID NO:20:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:20:

GTTCTGCAGC CGTTTCGATG GGCCTTCTC                                     29

(2) INFORMATION FOR SEQ ID NO:21:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:21:

GTTCTGCAGAA TGAGCTGCGC CAGTTG                                       27

(2) INFORMATION FOR SEQ ID NO:22:

(i) SEQUENCE CHARACTERISTICS:
        (A) LENGTH: 46 base pairs
        (B) TYPE: nucleic acid
        (C) STRANDEDNESS: single
        (D) TOPOLOGY: linear

```
    (ii) MOLECULE TYPE: Genomic DNA (xi) SEQUENCE DESCRIPTION: SEQ ID NO:22:

GAGACTGCAG GAGGTAATTC ATATGACCAC AAACTCCCCC TCAGAC                    46

(2) INFORMATION FOR SEQ ID NO:23:

(i) SEQUENCE CHARACTERISTICS:
         (A) LENGTH: 37 base pairs
         (B) TYPE: nucleic acid
         (C) STRANDEDNESS: single
         (D) TOPOLOGY: linear (ii) MOLECULE TYPE: Genomic DNA (xi) SEQUENCE DESCRIPTION: SEQ ID NO:23:

CAAGAGATCT AGTCGACCGG TGTTAGCAAC CCGATAC                              37
```